United States Patent [19]

Merril et al.

[11] Patent Number: 5,429,947
[45] Date of Patent: Jul. 4, 1995

[54] DIAGNOSING ALZHEIMER'S DISEASE AND SCHIZOPHRENIA

[76] Inventors: Carl R. Merril, 2 Winder Ct., Rockville, Md. 20850; Ginger Johnson, 2700 Martin Luther King Ave., SE., Washington, D.C. 20032; Hossein A. Ghanbari, U.S. MIND Diagnostics, Abbott Laboratories D-9MA, AP20, Abbott Park, Ill. 60064

[21] Appl. No.: 904,045

[22] Filed: Jun. 17, 1992

[51] Int. Cl.$^6$ .......................................... G01N 33/543
[52] U.S. Cl. ..................................... 436/518; 436/89; 436/161; 436/811
[58] Field of Search ................. 436/518, 516, 808, 86, 436/161, 811; 530/385

[56] References Cited

U.S. PATENT DOCUMENTS

| | | | |
|---|---|---|---|
| 4,666,828 | 5/1987 | Gusella | 435/6 |
| 4,801,533 | 1/1989 | Fudenberg | 435/7.24 |
| 4,892,814 | 1/1990 | Harrington et al. | 435/5 |

FOREIGN PATENT DOCUMENTS

| | | |
|---|---|---|
| 0444856 | 4/1991 | European Pat. Off. . |
| 9015331 | 12/1990 | WIPO . |

OTHER PUBLICATIONS

Wildenauer, D. B., et al., "Analysis of cerebrospinal fluid from patients with psychiatric and neurological disorders by two-dimensional electrophoresis: Identification of disease-associated polypeptides as fibrin fragments", *Electrophoresis*, vol. 12, pp. 487–492 (1991).
Myrick, J. E., et al., "Identification of haptoglobin alpha-2FF variants in mid-trimester maternal serum as potential markers for Down syndrome", *Appl. and Theoret. Electrophoresis*, vol. 1, pp. 233–241 (1990).
Harrington, M. G., et al., "Differences in Cerebrospinal Fluid Proteins between Patients with Schizophrenia and Normal Persons", *Clin. Chem.*, vol. 31, pp. 722–725 (1985).
Khachaturian, Z. S., "Diagnosis of Alzheimer's Disease", *Arch. Neurol.*, vol. 42, pp. 1097–1105 (1985).
Altstiel, H. D., et al., "Acute Phase Reactants in Alzhiemer's Disease", *Am. Coll. of Neuropsychopharm.*, 60 (1991).
Prohovnik, I., et al., "Looking under the Light: Prevalence of Alzheimer's Disease Histopathology in a Large Schizophrenic Autopsy Series", *Am. Coll. of Neuropsychopharm.*, 67 (1991).
Ruddudu et al. *Human Herod.* 35: 65–68 (1985).
Teige et al. *Human Genet.* 70:163–167 (1985).
Harlow & Sane (eds) in *Antibodies: A Laboratory Manual*, Cold Spring Harbor Laboratory, Ch. 14, pp. 584–585, 555–567 (1988).
Webster's Ninth New Collegiate Dictionary, 1990, p. 362.
Fisher Scientific, The Fisher Catalog, 1990, pp. 552, 557, 564, 566.

Primary Examiner—Esther M. Kepplinger
Assistant Examiner—Donna C. Wortman
Attorney, Agent, or Firm—Morgan & Finnegan

[57] ABSTRACT

A method for detecting elevated levels of the middle isoform of α-2 haptoglobin, α-2FS haptoglobin in bodily fluids of subjects with Alzheimer's disease and schizophrenia as compared with the α-2FS haptoglobin level in normal subjects. Fibrinogen fragments corresponding to proteins 127 and 128 are also found in elevated levels in such subjects. Elevated levels of specific haptoglobin proteins serve as a diagnostic marker for Alzheimer's disease and Schizophrenia.

5 Claims, 3 Drawing Sheets

DIAGNOSING ALZHEIMER'S DISEASE AND SCHIZOPHRENIA

FIELD OF INVENTION

This invention relates to methods of diagnosing Alzheimer disease and schizophrenia in subjects by detecting and measuring elevated levels of specific proteins in bodily fluids. The invention also relates to an in vitro diagnostic assay to assist in diagnosis of Alzheimer's disease and schizophrenia.

BACKGROUND OF THE INVENTION

Schizophrenia and Alzheimer's disease are major public health problems. The problems associated with these diseases are compounded by the lack of clinically useful, objective methods of diagnosis. This diagnostic deficiency reflects a lack of understanding of the pathophysiology involved.

Many diseases of the central nervous system (CNS), such as Alzheimer's disease and schizophrenia, have few objective physical or biochemical markers useful for diagnostic purposes in the living patient. Alzheimer's disease, the most common form of dementia affecting up to 15% of people over 65 years of age (Pfeffer et al., 1987 Am. J. Epidemiol, 125:420) can only be presumptively diagnosed by pathological examination of brain tissue in conjunction with a clinical history of dementia (Khachaturian 1985 Arch. Neurol., 42:1097). In the diagnosis of schizophrenia, the clinician is limited to aberrations of behavior. No generally accepted laboratory markers for either of these two diseases of the CNS have been found that would allow for diagnosis in a living subject. Cerebrospinal fluid (CSF), which can be obtained by lumbar puncture, provides a source of proteins which may, in part, reflect abnormal CNS metabolism.

In a search for protein variations in Alzheimer's disease and schizophrenia, high resolution two-dimensional protein electrophoresis (O'Farrell, 1975 J. Biol. Chem., 250:4007; Hochstrasser et al., 1988 Anal. Biochem., 173:424) was employed combined with silver staining (Merril and Harrington, 1984 Clin. Chem., 30:1938) and computer-assisted image analysis (Olson and Miller, 1988 Anal. Biochem., 169:49). These techniques allowed screening of an average of 1,000 proteins per gel containing 40 $\mu$l of CSF or 10 $\mu$g of protein. These methods of analysis provided the ability to detect changes in a protein's charge, mass, and/or concentration which might be the result of mutational effects, post-translational modifications, or variations in protein metabolism.

One group of proteins associated with such disorders are proteins produced in acute-phase reactions. This family of protein's expression can be dramatically increased by a variety of insults including infectious diseases, leukemia, Down's Syndrome, and others. One such protein, haptoglobin, is known to increase in the plasma in a number of acute and chronic inflammations (Koy, 1974 Acute-Phase Reactions, In: Allison, A. C. (ed). Structure and function of plasma proteins. Plenum Press, New York, pp. 73–133). Another acute phase protein, fibrinogen, is synthesized in the liver and is increased concentration in plasma after infection or injury. Two proteins, proteins 127 and 128 which have been identified as fragments of fibrin (Wildenauer et al., 1991 Electrophoresis, 12:487), have also been found in elevated levels in spinal fluid from schizophrenic patients (Harrington et al., 1985 Clin. Chem., 31:722; Harrington et al., 1986 N. England. J. Med., 315:279; Wildenauer et al., 1988 Proc. Int. 2D Electroph. Conf., Verlagsgesellschaft, Vienna p. 212–218; Wildenauer et al., 1991 Electrophoresis, 12:487).

Elevated levels of other acute phase proteins are associated with CNS disorders. Altstiel et al. (1991 Amer. Coll. of Neuropsychopharm., 60) have shown an increased hepatic synthesis of $\alpha_1$-antichymotrypsin and C reactive protein in Alzheimer's disease patients. They also describe the presence of $\alpha_1$-antichymotrypsin and C reactive protein in the plaques of Alzheimer's disease patients' brains. These proteins can be stimulated by the cytokines interleukin-1 and interleukin-6, which are produced by reactive human astrocytes. In this regard, serum interleukin-6 has been reported as elevated in some schizophrenic patients (Shinani et al., 1991 Life Sciences, 49:661). If acute phase proteins play a role in the pathophysiology of both of these diseases, one might predict an increased incidence of Alzheimer's disease in schizophrenic patients. Prohovnik et al. (1991 Amer. Coll. of Neuropsychopharm., 67) in a review of 1,046 neuropathological records found that the prevalence of a neuropathological diagnosis consistent with Alzheimer's disease was considerably higher in schizophrenic patients than that expected for the general population.

It is an object of the present invention to define the protein variations associated with two diseases of the CNS, Alzheimer's disease and schizophrenia.

SUMMARY OF THE INVENTION

The present invention relates to a method of diagnosis of Alzheimer's disease and schizophrenia by detection of elevated levels of specific proteins in a biological sample.

The present invention also relates to the use of such proteins as diagnostic markers for central nervous system disorders, such as Alzheimer's disease and schizophrenia.

The present invention also encompasses methods of detecting and measuring elevated levels of the middle isoform of $\alpha$-2 haptoglobin, $\alpha$-2FS haptoglobin in subjects suspected of having diseases where this molecule is found in elevated levels such as Alzheimer's disease and schizophrenia. Such methods are useful for diagnosis of diseases where elevated levels of $\alpha$-2 haptoglobins are found and for monitoring the progression of such diseases.

Such methods can also be useful for monitoring the efficacy of therapeutic agents during the course of treatment of central nervous system disorders such as Alzheimer's disease and schizophrenia, where elevated levels of $\alpha$-2 haptoglobins are found.

BRIEF DESCRIPTION OF THE DRAWINGS

These and other objects, features, and many of the attendant advantages of the present invention will be better understood from the following detailed description when considered in connection with the accompanying drawings wherein.

DETAILED DESCRIPTION OF THE INVENTION

Figure 1:
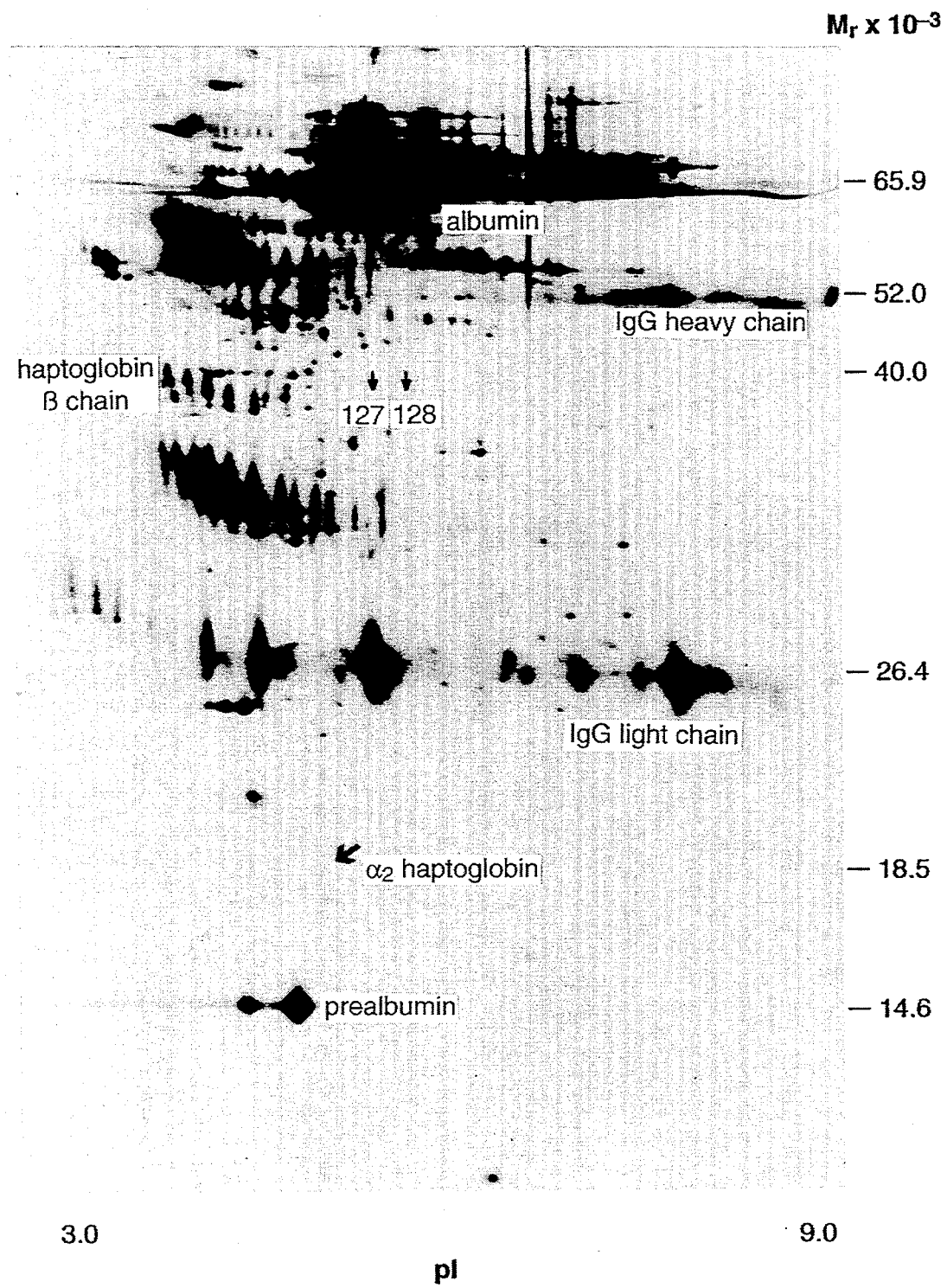
FIG. 1 is a representative high resolution two-dimensional CSF electrophoretogram.

The cerebrospinal fluid protein patterns of Alzheimer's disease and schizophrenic patients were analyzed by high resolution two dimensional electrophoresis. Improvements in this technique now allow visualization and evaluation of at least five times as many proteins in CSF. In this study, the middle isoform of a α-2 haptoglobin, α-2FS haptoglobin (Myrick et al., 1990 Appl. and Theor. Electroph., 1:233) was found to be elevated in the spinal fluid from a group of patients with schizophrenia and in a group of patients with Alzheimer's disease. The cause of the increased concentration of α-2FS haptoglobin in the CSF of these patients is not known at this time.

Some of the possible causes of this elevation may include: medication, iron deficiency, or an as yet undefined pathophysiological process that is common to both of these disorders. The possibilities have been eliminated by experimentation as described below, in order to establish the cause of the elevated protein levels as linked to Alzheimer's disease and schizophrenia.

As many of the schizophrenic patients in this study were receiving haloperidol therapy, the effect of this medication on CSF high resolution two dimensional protein patterns in a separate experiment was evaluated (Johnson et al., 1992 Appl. and Theor. Electroph., 3:21 in press). Ten schizophrenic patients during haloperidol therapy and after an average of 6 weeks of placebo therapy were examined. While it was expected to find some protein alterations, it was a surprise to find an average decrease of 21% in the total number of proteins which could be visualized in the CSF of patients treated with haloperidol as compared with the number of CSF proteins observed when the same patients were treated with placebo. These observations effectively rule out haloperidol as the cause of an increased concentration of α-2FS haptoglobin in the schizophrenic patients.

An increase in α-2FS haptoglobin in the CSF of patients with Alzheimer's disease and schizophrenia could be caused by an iron deficiency. In the plasma, haptoglobin is elevated during periods of iron deficient metabolism. However, it is unlikely that the increase observed in α-2FS haptoglobin was due to iron deficiency as the majority of the patients in this study were hospitalized and routine complete blood counts did not demonstrate significant hematologic abnormalities.

In the current study proteins 127 and 128 were found in the CSF of patients with Alzheimer's disease as well as in the CSF of schizophrenic patients. While this evidence suggests that there may be an acute phase response in these diseases, there are some complicating factors, such as the fact that only the middle isoform of α-2 haptoglobin, α-2FS haptoglobin, was elevated, and only fragments of fibrinogen were detected. The preferential presence of the α-2 form of haptoglobin in these patients may indicate the presence of a genetic component in these observations. Further studies are being directed toward the elucidation of a genetic linkage between a genetic locus for schizophrenia and polymorphic DNA markers in the areas of interest. Another possible explanation for the presence of these polypeptides in the patients is that they represent a differential CSF clearance of the fragments of acute phase proteins.

The elevated levels of α-2 haptoglobin protein can be detected by various means including, for example, using an immunoblot. It may be necessary for the samples to be concentrated using conventional techniques, such as ultrafiltration, freeze drying, evaporation, reverse osmosis, etc. The preferred concentration is about 0.5 mg/ml. Those skilled in the art will appreciate that the protein concentration desired can vary depending upon the sensitivity of the reporter system and affinity of the antibodies as well as the quality of the samples. Thus, the desired concentration can vary depending upon these factors.

Although the proteins identified herein were found in elevated levels in the cerebrospinal fluids of Alzheimer's disease and schizophrenic patients, the proteins are in fact found predominantly in the blood. This will allow diagnosis of Alzheimer's disease and schizophrenia by a simple blood test. A variety of other biological samples comprising bodily fluids and tissues, such as blood, plasma, serum, cerebrospinal fluids, brain tissue, liver tissue, urine and the like can be used in the assay of the present invention.

Figure 2A:
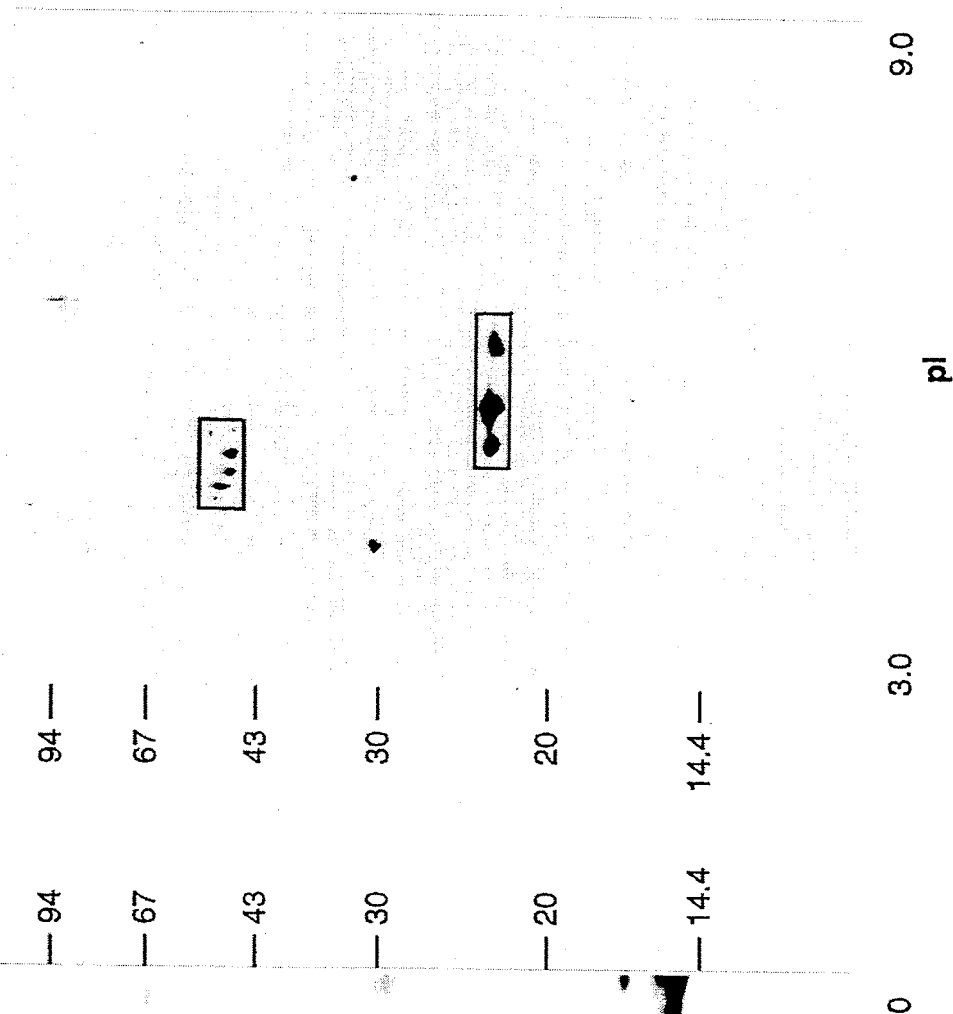
FIG. 2 is a Western blot showing visualization of $\alpha_2$-haptoglobin in CSF from a patient with schizophrenia detected with a polyclonal antibody to native haptoglobin.
Figure 2B:
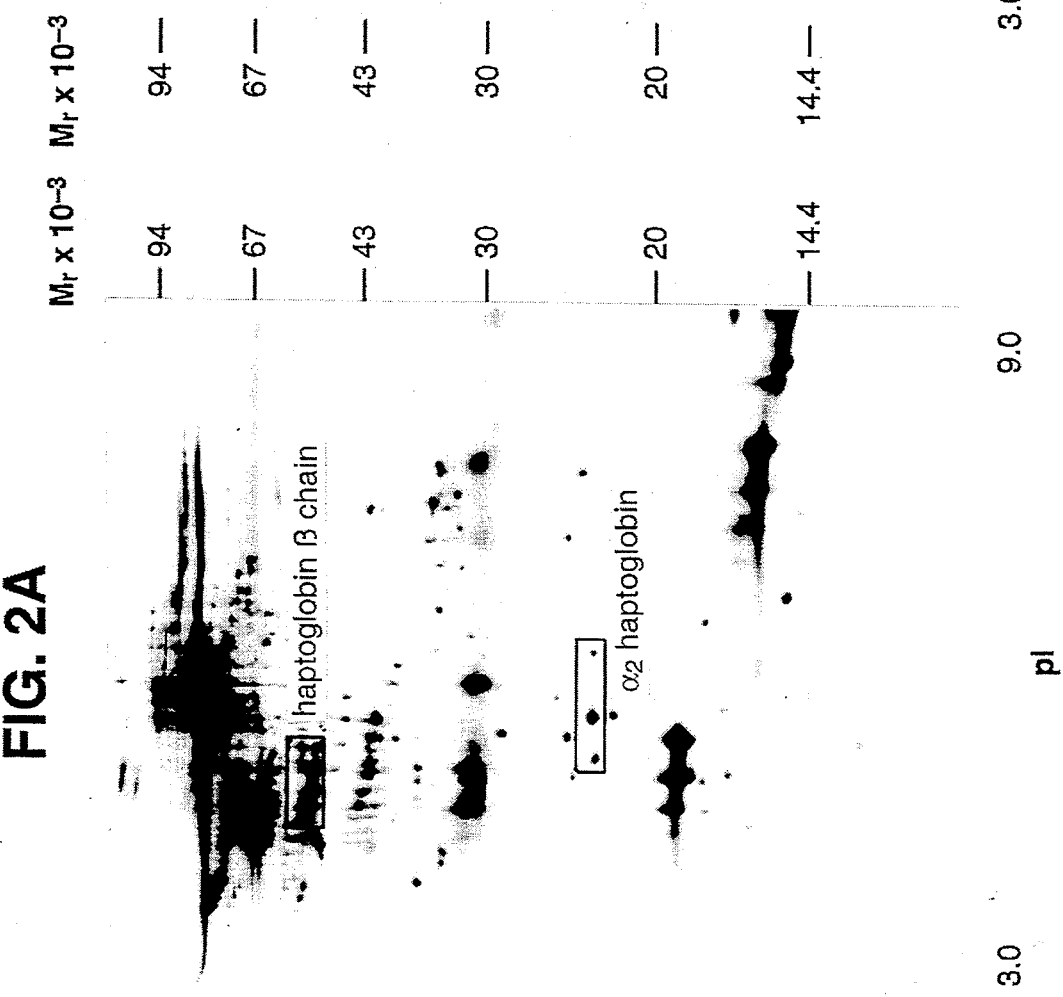

In a preferred embodiment, proteins of the biological sample are separated by two-dimensional gel electrophoresis, and visualized by silver staining. Silver staining of such separated proteins affords several advantages for detection and quantitation of α-2FS haptoglobin. Two-dimensional gel electrophoresis allows separation of the various isoforms of haptoglobin. The silver staining method of visualization can detect as little as 0.1 ng protein, making it the most sensitive staining technique currently available. α-2FS haptoglobin can be directly quantitated from silver stained gels by computer assisted laser densitometric scanning of the stained gel.

α-2FS Haptoglobin specific antibodies can be generated against various peptides corresponding to subsequences of the α-2FS haptoglobin gene using conventional techniques known to one skilled in the art (Yang et al 1983 Proc. Natl. Acad. Sci., 80:5875). Alternatively, α-2FS haptoglobin specific antibodies can be generated from an isolated protein as seen in FIG. 2 by methods well known to one skilled in the art. It is also within the scope of this invention to use monoclonal antibodies or immunoreactive fragments thereof to identify the presence of elevated levels of α-2FS haptoglobin, protein 127 and 128, and fragments thereof that might exist in the disease state when compared to results obtained from normal samples. Monoclonal antibodies can be generated using the standard hybridoma technology such as that described in U.S. Pat. No. 4,196,265 and Kohler et al. (Nature, 256:495, 1975).

The sensitivity of detection by immunoblot is increased about three-fold by incubating the haptoglobin-specific-antibody complex with a detector system which comprises two detector reagents at two different dilutions after concentrating protein from the samples to a desired level. Following incubation with rabbit anti-human haptoglobin antibody, the next incubation should be with a dilution of the first detector reagent at a dilution determined empirically based on its titer and affinity for the initial antibody. Typically, the dilution of the first detector reagent is about one to about six-fold less than that of the second detector reagent. The second detector is used to amplify the signal due to its affinity for the first detection system. The increased sensitivity appears to be related to the presence of additional complexes that form first from a goat anti-rabbit antibody followed by incubation with a rabbit anti-goat antibody.

Those skilled in the art will appreciate that the detector system can include any reagent or combination of reagents suitable for detecting proteins in an immunoblot format. Typically, an anti-antibody coupled to a reporter is used as a detector reagent. Reporters include, for example, enzymes, such as, horseradish peroxidase and alkaline phosphatase, radioisotopes, chemiluminescent, fluorogenic or electrochemical materials. Various coupling techniques are known to those skilled in the art.

The observed elevation of the acute phase proteins α-2FS haptoglobin and fragments of fibrinogen in the CSF of subjects may provide diagnostic markers for the Alzheimer and schizophrenia disease states. A diagnostic assay can be carried out by use of an isoelectric focusing step (Righetti, 1983, "Isoelectric Focusing: Theory, Methodology and Applications." Elsevier, Amsterdam; Tiege et al., 1985 Hum. Genetics, 70:163) the methods of which are hereby incorporated by reference, to separate the different isoforms of haptoglobins in the sample, followed by a standard immunoassay using a human haptoglobin antiserum, detectable by a labeling anti-antibody. Techniques available for such an immunoassay will be apparent to one skilled in the art.

These methods include but are not limited to methods which immobilize the antibody or antigen on a solid matrix as well as methods carried out in solution. The methods can be conducted by direct detection of an immune complex, such as when the primary antibody is labelled with a reporter or by indirect detection of the immune complex such that a secondary or tertiary detection molecule is labeling with a reporter. This latter technique can afford amplification of the detectable immune complex.

Another embodiment for diagnosis of Alzheimer's disease and schizophrenia entails detecting elevated levels of haptoglobins using a sandwich immunoassay. A sample is obtained and contacted with a suitable amount of first antibody to produce a complex. The contact typically involves adding the sample to a solid matrix coated with the first antibody. The complex which results from contacting the sample with the first antibody is separated from the sample by elution. However, other methods of recovery may be employed. The recovered complex is contacted with at least one second antibody directed to an antigenic determinant on the antigen and capable of binding to the antigen in the complex. The antigenic determinant to which the second antibody is directed may be the same one as that to which the first antibody is directed due to the multiepitopic nature (i.e. repeating epitopes) of the antigenic entity. The conditions for effecting such contact are known to those skilled in the art.

The first or second antibody may be made detectable by attaching an identifiable label to it. In a preferred embodiment, the second antibody is made detectable. The antibody preferably is made detectable by attaching to it an enzyme conjugated to an appropriate substrate which, in turn, catalyzes a detectable reaction. The enzyme may be horseradish peroxidase, beta-galactosidase or alkaline phosphatase. Other means of detection of the antibody include attaching a fluorescent or radiolabel thereto. Alternatively, the antibody may be detected by use of another antibody directed to it, the other antibody being labeling or having an enzyme substrate bound to it.

The presence of the detectable antibody bound to the antigen of the complex consisting of antigen bound to the first and second antibody may be readily detected using well-known techniques. Thus, if the detectable antibody is linked to an enzyme conjugated to an appropriate substrate, the optical density of the detectable bound antibody is determined using a spectrophotometer. If the detectable antibody is fluorescently labeling, the fluorescent emission may be measured or detected using a fluorometer technique. In a similar manner, if the detectable antibody is radioactively labeling, the bound antibody may be detected using a radioactivity detection techniques. By comparison the results obtained using the above-described methods on the test sample with those obtained using the methods on a control sample, the presence of elevated levels of α-2FS haptoglobin may be determined.

Utilization of the methods of the present invention is advantageous over prior art methods because the present invention provides simple, sensitive, specific methods for detecting α-2FS haptoglobin. The configuration of this assay minimizes complications caused by the cross-reactants from cerebrospinal fluids.

EXAMPLE 1

Qualitative Analysis of Haptoglobins

Sample Preparation. CSF samples were obtained by lumbar puncture from Alzheimer's and schizophrenic patients (meeting DSM III criteria, Spitzer, 1980, American Psychiatric Association: Diagnostic and Statistical Manual of Mental Disorders, Third edition, Amer. Psychiatric Assoc., Washington, D.C. pp. 101–198) and controls. CSF samples (100 $\mu$l) were denatured in 30 $\mu$l of an isoelectric preparative (IP) solution containing 0.20 g SDS, 0.23 g DTT, 5% (w/v) ampholytes (BDH; Hoefer) in a 1:4 ratio of pH 4—4 and pH 3.5–10, 0.2 g CHAPS, and 2.0 ml glycerol brought a 10 ml with deionized water, followed by heating at 95° C. for 4 minutes. Protein concentrations were determined by the method of Lowry et al. (1951 J. Biol. Chem., 193:265) the method of which is hereby incorporated by reference.

High Resolution Two-Dimensional Gel Electrophoresis. The 2D procedure was performed as described by Hochstrasser et al. (1988 Anal. Biochem., 173:424) incorporated herein by reference with minor revisions. CSF proteins in IP solution (60 $\mu$l) were separated by charge in the first dimension on polyacrylamide gels in 1.4 mm i.d. glass capillary tubes. The gels contained 10 g urea, 7.0 ml deionized water, 2.5 ml diacrylpiperazine (PDA TM, BioRad)/acrylamide stock solution (300 g acrylamide and 8 g PDA in one liter deionized water), 1 ml of a CHAPS/NP-40 solution containing 0.3 g CHAPS, 900 $\mu$l deionized water and 100 $\mu$l NP-40), 800 $\mu$l pH 3.5–10 ampholines (BDH TM; Hoefer), 20 $\mu$l TEMED, and 40 $\mu$l 10% ammonium persulfate. Isoelectric focusing was performed in a model 175 isoelectric chamber (BioRad) with voltage supplied by a 3000Xi programmable power supply (BioRad). Focusing was initiated with a constant voltage of 200 V for 2 h, followed by 500 V for 5 h, and finally 800 V for 12 h. Capillary tube gels were extruded from the glass tubes and rinsed with 150 $\mu$l of transfer solution containing 8 $\mu$l of a stock bromophenol blue solution (0.5 g/liter), 20 ml of a stock Tris-HCl pH 6,8 buffer (0.5 mol/liter), 72 ml deionized water. Tube gels were then loaded onto the second dimension polyacrylamide slab gels that contained 12% acrylamide, 0.4M Tris-HCl (pH 8.8), 0.03% sodium thiosulfate, 0.32% PDA, 0.45% 1,4-dimethylpiperazine, and 0.06% ammonium persulfate. Slab gels were loaded into a PROTEAN II ™ chamber (BioRad), a SDS-PAGE electrophoresis tank, and the proteins were separated by mass with a constant current of 40 mA per gel until the dye front reached the bottom of the gel (approximately 4 h).

Silver Staining. Gels were silver stained with ammoniacal silver nitrate using a method introduced in 1979 (Switzer et al. 1979 Anal. Biochem., 98:231; Merril et al. 1979 Proc. Natl. Acad. Sci., 76:4335) as modified by Hochstrasser et al. (1988 Anal. Biochem., 173:424) incorporated herein by reference. Following electrophoresis, proteins were fixed in the gels with an ethanol/acetic acid/deionized water solution (40/10/50) for 1 h followed by an ethanol/acetic acid/deionized water solution (5/5/90) overnight. Gels were then soaked in a solution containing 5% glutaraldehyde for 30 minutes. The gels were washed extensively ($3\times20$ minutes, then overnight) with deionized water. Silver staining was initiated by soaking the gels for 30 minutes in an ammoniacal silver solution (6 g silver nitrate dissolved in 30 ml deionized water slowly mixed into a solution containing 160 ml deionized water, 10 ml concentrated ammonium hydroxide, and 1.5 ml 10N sodium hydroxide diluted to a final volume of 750 ml). Protein images were developed in a solution containing 0.1 g citric acid and 1 ml of concentrated formaldehyde in 1 liter of deionized water. Image development was stopped in a 5% (v/v) acetic acid/deionized water solution. Gels were rinsed in deionized water and stored in zip-lock plastic bags.

Silver stained electrophoretograms of CSF proteins from 13 Alzheimer's disease (AD) patients, 15 age matched controls, 28 schizophrenic (SCZ) patients, and 10 age matched controls were analyzed with the ELSIE computer program (Olson and Miller, 1988 Anal. Biochem., 169:49). The electrophoretic separation in FIG. 1 was performed with 40 µl of CSF from a patient with schizophrenia. The $\alpha$-2FS haptoglobin spot, highlighted by the arrow, is increased in concentration when compared with normal controls. The positions of proteins 127 and 128 are indicated by the labeling arrows. A polypeptide (Mr 18,000; pI 6.5) was present in increased concentration in both Alzheimer's disease and schizophrenic patients when compared to the appropriate controls (FIG. 1). This protein was identified as an isoform of a $\alpha$-2 haptoglobin by electroblotting and immunodetection with polyclonal antibody to native haptoglobin (FIG. 2). As this $\alpha$-2 haptoglobin isoform appears in the same gel region as the isoform provisionally identified as the $\alpha$-2FS by Myrick et al. (1990 Appl. and Theor. Electroph., 1:233) the same nomenclature is used here.

Proteins 127 and 128 (40,000 Mr, and pI 5.7 and 5.9 respectively) were also found in the CSF from some of the Alzheimer and schizophrenic patients (FIG. 1). These proteins were originally observed in 31.5% of schizophrenic patients, and in none of the controls (Harrington et al. 1985 Clin. Chem., 31:722). The results of the current study are consistent with these original finding. Proteins 127 and 128 were present in 27% of the schizophrenic patients in the current study. Proteins 127 and 128 were also found in 23% of Alzheimer's disease patients. Only one of the 25 control CSF samples used in this study was positive for proteins 127 and 128.

EXAMPLE 2

Quantitation of Elevated Haptoglobins

Gel Analysis. The 2D gel electrophoretograms were scanned with a Photometrics ™ Series 200 CCD camera system and analyzed on a Sun Microsystems ™ 4/260 computer with the ELSIE program developed by Olson and Miller (1988 Anal. Biochem., 169:49), incorporated herein by reference. This computer program uses an algorithm to distinguish polypeptide spots from background uses an algorithm to distinguish polypeptide spots from background staining and aids in the quantitative and qualitative analysis of 2D gels. Normalization for variations in scanning and silver staining were performed by comparing the total integrated density of the gels. Protein values are reported as the percent integrated density value of the protein of interest compared on the gel. The presence or absence of proteins 127 and 128 (Harrington et al., 1985 Clin. Chem., 31:722) was evaluated visually.

The increase in a $\alpha$-2FS haptoglobin was not accompanied by increased $\alpha$-1 haptoglobin. Quantitation of $\beta$-haptoglobin was not possible in this study as it was saturated on our silver stained 2D gels.

Figure 3A:
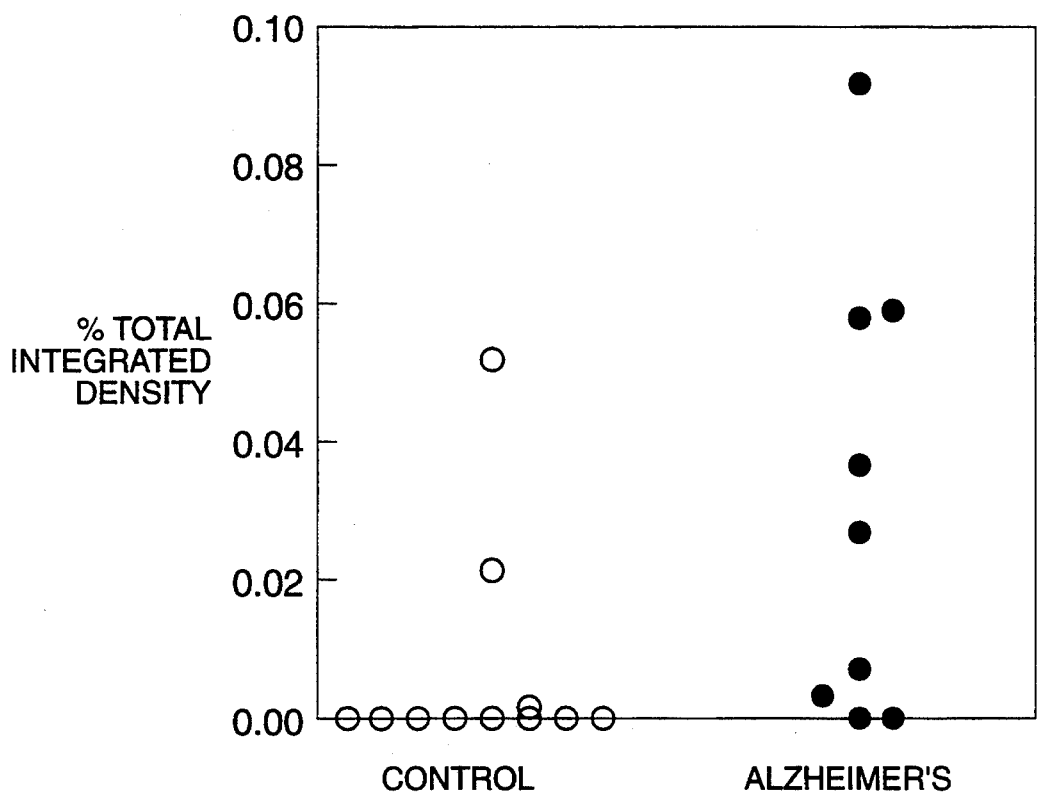
FIG. 3A and 3B are comparative charts illustrating CSF α-2FS haptoglobin densities in patients and controls.
Figure 3B:
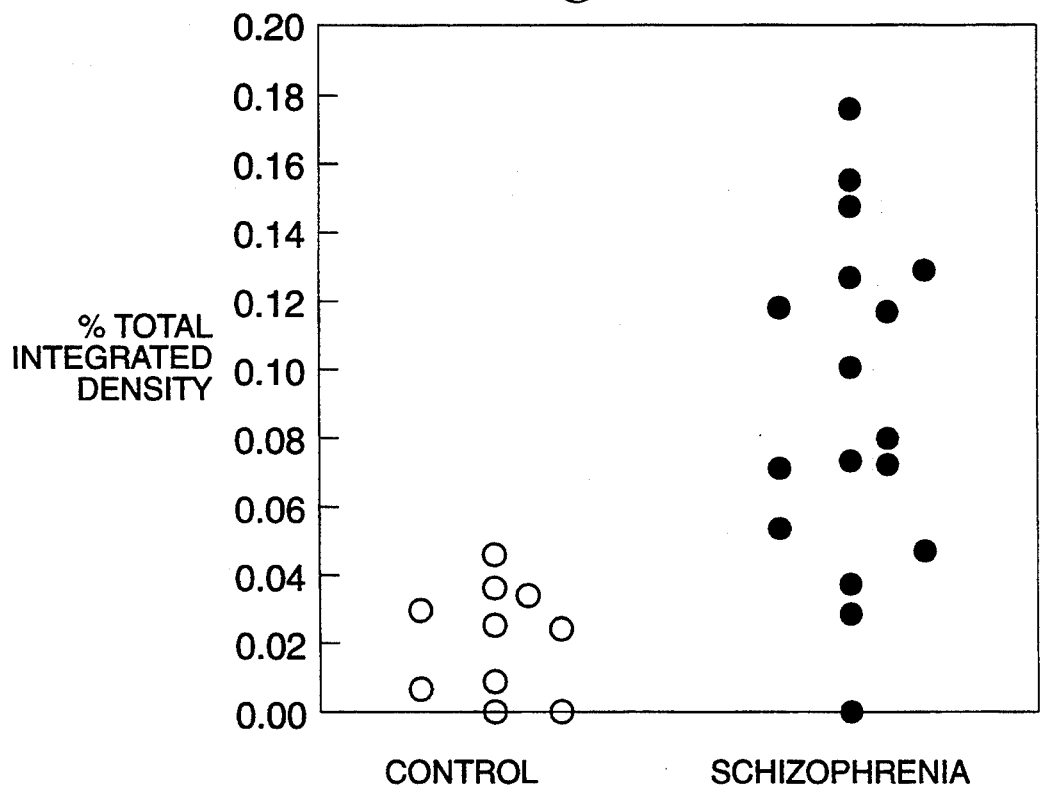

There was an increase of 6.8-fold in the mean percent integrated density value of a $\alpha$-2FS haptoglobin when comparing CSF samples from Alzheimer's disease patients with those from controls (mean % density value=$0.048\pm0.049$ for the AD patients; n=9 and $0.007\pm0.017$ for the controls; n=11, p<0.025 (FIG. 3A). This protein was increased 4.4-fold in the CSF of schizophrenics when compared with age-matched controls (mean % density value=$0.087\pm0.048$ for the patients with schizophrenia; n=17 and $0.021\pm0.016$ for the controls; n=10, p<0.001) (FIG. 3B). In a second set of samples from schizophrenic patients and controls, from an independent source, we found a similar increase in a $\alpha$-2FS haptoglobin (mean % density value=$0.072\pm0.62$ for the patients with schizophrenia; n=10 and $0.025\pm0.024$ for the controls; n=7, p<0.05).

Statistical Analysis. Student's t-tests were used to test for significant differences between the percent integrated density values of $\alpha$-2 haptoglobin and other constituents in the CSF samples of schizophrenic and Alzheimer's disease patient with their respective controls.

EXAMPLE 3

Immuno-Analysis of Protein Levels

Protein Electroblotting. The method used was originally described by Towbin et al. (1979 Proc. Natl. Acad. Sci. 76:4350) and modified by Anderson et al. (1982 Electrophoresis 3:135) hereby incorporated by reference. Following 2D separation of proteins, gels were soaked for thirty minutes in a buffered solution containing 0.25M Tris (pH 8.3) and 1.92M glycine in one liter deionized water. Proteins were then electroblotted onto polyvinyledene difluoride (PVDF) membrane (Immobilion ™, Millipore) in a TE SERIES TRANSPHOR electrophoresis unit (Hoefer Scientific), a protein electroblotting tank, filled with the 0.25M Tris buffer described above at 1.2 A (as supplied by a Model 200/2.0 BioRad power supply) for 3 h. Buffer temperature was maintained at 8° C. throughout the entire run.

Immune Detection of Proteins. Immediately following electroblotting, transfer membranes were placed protein side up in 33 mm i.d.×300 mm long glass tubes (Robbins Scientific) with one to two membranes per tube. Non-specific sites were blocked by immersing the membranes in 50 ml of blocking solution containing 10 mM Tris-HC1 (pH 7.0), 150 mM NaCl, and 3% w/v bovine serum albumin overnight at room temperature on an incubation rotor (Robbins Scientific). Membranes were then washed twice (20 minutes each) with 50 ml of Tris-buffered saline (10 mM Tris-HC1, pH 7.0 and 150 mM NaCl). Each electroblotted membrane was incubated in 25 ml of a 1:500 dilution of horseradish peroxidase-labeling sheep anti-human haptoglobin antiserum (Serotec) in blocking solution for 4 hours. Membranes were washed twice with Tris-buffered saline for 20 minutes, then overnight. Immune complexes were detected using the Western blotting detection ENHANCED CHEMILUMINESCENCE (ECL) (Amersham), a Western blot immunodetection system. This system is stimulated to emit light by the immobilized antigens when they are conjugated directly or indirectly with the horseradish peroxidase-labeling antibodies.

It is understood that the examples and embodiments described herein are for illustrative purposes only and that various modifications or changes in light thereof will suggest to persons skilled in the art to be included within the spirit and purview of this application and scope of the appended claims.

We claim:

1. A method of screening for Alzheimer's disease or schizophrenia in a subject comprising analyzing separated haptoglobins of a cerebrospinal fluid sample from a subject for an elevated level of $\alpha$-2FS haptoglobins compared to a normal level of $\alpha$-2FS haptoglobin, wherein the elevated level of $\alpha$-2FS indicates a positive result in said screening method for Alzheimer's disease or schizophrenia.

2. The method of claim 1 wherein protein separation in said sample is obtained by electrophoresis.

3. The method of claim 2, wherein protein is detected by silver staining.

4. The method of claim 2, wherein $\alpha$-2FS haptoglobin is detected by contacting the separated haptoglobins with an antibody that specifically binds human haptoglobins to form an immune complex and detecting the amount of immune complex formed between $\alpha$-2FS haptoglobin and said antibody as an indication of the level of $\alpha$-2FS haptoglobin in said sample.

5. The method of claim 1, further comprising detecting protein 127 and protein 128 in said sample.

* * * * *